United States Patent [19]

Braun et al.

[11] Patent Number: 4,778,460

[45] Date of Patent: Oct. 18, 1988

[54] MULTILAYER NONWOVEN FABRIC

[75] Inventors: Ralph V. Braun, Roswell; Jon R. Butt, Woodstock; Robert J. Phelan, Woodstock, all of Ga.; Lin-Sun Woon, Appleton, Wis.

[73] Assignee: Kimberly-Clark Corporation, Neenah, Wis.

[21] Appl. No.: 785,369

[22] Filed: Oct. 7, 1985

[51] Int. Cl.$^4$ ............................................. A61F 13/16
[52] U.S. Cl. ....................... 604/380; 428/172; 428/198; 428/212; 428/284; 428/286; 428/296; 428/298; 428/397; 428/913; 604/370
[58] Field of Search ............... 428/172, 212, 284, 286, 428/298, 397, 913, 198, 296; 604/370, 380

[56] References Cited

U.S. PATENT DOCUMENTS

| Re. 31,599 | 6/1984 | Rasen et al. | 156/167 |
|---|---|---|---|
| 1,786,669 | 12/1930 | Manning | 19/308 |
| 2,121,802 | 6/1938 | Kleist et al. | 49/1 |
| 2,188,332 | 1/1940 | Carothers | 91/68 |
| 2,331,945 | 10/1943 | Pazsiczky | 49/1 |
| 2,336,743 | 12/1943 | Manning | 156/167 |
| 2,336,745 | 12/1943 | Manning | 156/181 |
| 2,411,660 | 11/1946 | Manning | 156/175 |
| 2,437,263 | 3/1948 | Manning | 18/8 |
| 2,456,922 | 12/1948 | Cogovan | 154/45.9 |
| 2,508,462 | 5/1950 | Marshall | 18/8 |
| 2,522,527 | 9/1950 | Manning | 156/175 |
| 2,604,667 | 7/1952 | Hebeler | 18/54 |
| 2,620,853 | 12/1952 | Boese | 154/33 |
| 2,644,779 | 7/1953 | Manning | 154/90 |
| 2,688,380 | 9/1954 | MacHenry | 156/180 |
| 2,810,426 | 10/1957 | Till et al. | 154/27 |
| 2,825,120 | 3/1958 | Smith | 28/82 |
| 2,861,319 | 11/1958 | Breen | 428/373 |
| 2,945,739 | 7/1960 | Lehmicke | 18/54 |
| 3,028,623 | 4/1962 | Labino | 18/2.5 |
| 3,063,459 | 11/1962 | Coates et al. | 128/290 |
| 3,109,220 | 11/1963 | McKinney et al. | 139/420 |
| 3,109,278 | 11/1963 | Gibson, Jr. | 57/140 |
| 3,117,906 | 1/1964 | Tanner | 161/177 |
| 3,154,836 | 11/1964 | Hoag, Jr. et al. | 28/64 |
| 3,164,949 | 1/1965 | Pitzl | 57/140 |

(List continued on next page.)

FOREIGN PATENT DOCUMENTS

| 12860 | 1/1980 | Japan . |
| 128006 | 10/1980 | Japan . |
| 42980 | 4/1981 | Japan . |
| 107044 | 8/1981 | Japan . |
| 50001 | 11/1981 | Japan . |
| 42916 | 3/1982 | Japan . |
| 61712 | 4/1982 | Japan . |
| 25645 | 5/1982 | Japan . |
| 37961 | 8/1983 | Japan . |
| 36741 | 2/1984 | Japan . |
| 47446 | 3/1984 | Japan . |
| 94609 | 3/1984 | Japan . |
| 204919 | 11/1984 | Japan . |
| 228019 | 11/1984 | Japan . |
| 223314 | 12/1984 | Japan . |
| 228042 | 12/1984 | Japan . |
| 4575 | 1/1985 | Japan . |
| 134012 | 8/1985 | Japan . |
| 185810 | 9/1985 | Japan . |
| 51565 | 11/1985 | Japan . |
| 12907 | 1/1986 | Japan . |
| 83307 | 4/1986 | Japan . |
| 83308 | 4/1986 | Japan . |
| 83309 | 4/1986 | Japan . |

OTHER PUBLICATIONS

Scardino, Frank and Frank Ko, "Engineering Properties of Fibers for Nonwoven Fabrics," *Nonwovens Industry*, Apr. 83, pp. 18–22.

Primary Examiner—James J. Bell
Attorney, Agent, or Firm—Patrick C. Wilson

[57] ABSTRACT

A multilayer nonwoven fabric is disclosed which comprises at least two layers of nonwoven web. Each nonwoven web comprises a plurality of monofilaments of a thermoplastic material. In at least one of the webs the monofilaments have a bilobal cross-section. Preferably, the fabric includes two layers of nonwoven web with the monofilaments of the first web having the bilobal cross-section and the monofilaments of the second web having a trilobal or branched cross-section.

54 Claims, 3 Drawing Sheets

U.S. PATENT DOCUMENTS

| | | | |
|---|---|---|---|
| 3,219,739 | 11/1965 | Breen et al. | 264/177 |
| 3,266,969 | 8/1966 | Makansi | 161/63 |
| 3,297,807 | 1/1967 | Settele | 264/171 |
| 3,303,169 | 2/1967 | Pitzl | 260/78 |
| 3,314,840 | 4/1967 | Lloyd et al. | 156/167 |
| 3,322,607 | 5/1967 | Jung | 161/67 |
| 3,360,421 | 12/1967 | Sands | 161/63 |
| 3,366,722 | 1/1968 | Tessier | 264/168 |
| 3,379,811 | 4/1968 | Hartmann et al. | 264/210 |
| 3,396,071 | 8/1968 | Couzens | 161/150 |
| 3,402,548 | 9/1968 | Wininger, Jr. et al. | 57/140 |
| 3,420,235 | 1/1969 | Harmon | 128/290 |
| 3,441,468 | 4/1969 | Siggel et al. | 264/12 |
| 3,492,389 | 1/1970 | Port et al. | 264/147 |
| 3,502,763 | 3/1970 | Hartmann | 264/210 |
| 3,508,390 | 4/1970 | Bagnall et al. | 57/140 |
| 3,509,009 | 4/1970 | Hartmann | 161/150 |
| 3,528,129 | 9/1970 | Hartmann | 18/8 |
| 3,533,904 | 10/1970 | Jurkiewitsch | 161/173 |
| 3,547,763 | 12/1970 | Hoffman, Jr. | 161/173 |
| 3,554,854 | 1/1971 | Hartmann | 161/150 |
| 3,630,816 | 12/1971 | Parker | 161/72 |
| 3,692,618 | 9/1972 | Dorschner et al. | 161/72 |
| 3,758,373 | 9/1973 | Rich | 264/12 |
| 3,837,995 | 9/1974 | Floden | 161/150 |
| 3,841,953 | 10/1974 | Lohkamp et al. | 161/150 |
| 3,855,045 | 12/1974 | Brock | 428/198 |
| 3,855,046 | 12/1974 | Hansen et al. | 161/150 |
| 3,949,127 | 4/1976 | Ostermeier et al. | 428/137 |
| 3,968,307 | 7/1976 | Matsui et al. | 264/171 |
| 4,013,816 | 3/1977 | Sabee et al. | 428/288 |
| 4,039,711 | 8/1977 | Newman | 428/286 |
| 4,041,203 | 8/1977 | Brock et al. | 428/157 |
| 4,041,689 | 8/1977 | Duncan et al. | 57/140 J |
| 4,054,709 | 10/1977 | Belitsin et al. | 428/397 |
| 4,085,175 | 4/1978 | Keuchel | 264/51 |
| 4,091,140 | 5/1978 | Harmon | 428/288 |
| 4,100,319 | 7/1978 | Schwartz | 428/171 |
| 4,107,364 | 8/1978 | Sisson | 428/196 |
| 4,211,816 | 7/1980 | Booker et al. | 428/296 |
| 4,287,251 | 9/1981 | King et al. | 428/198 |
| 4,304,234 | 12/1981 | Hartmann | 128/287 |
| 4,315,965 | 2/1982 | Mason et al. | 428/198 |
| 4,333,979 | 6/1982 | Sciaraffa et al. | 428/179 |
| 4,340,563 | 7/1982 | Appel et al. | 264/210 |
| 4,350,006 | 9/1982 | Okamoto et al. | 57/250 |
| 4,363,845 | 12/1982 | Hartmann | 428/198 |
| 4,379,192 | 4/1983 | Wahlquist | 428/156 |
| 4,405,297 | 9/1983 | Appel et al. | 425/725 |
| 4,434,204 | 2/1984 | Hartman et al. | 428/198 |
| 4,436,780 | 3/1984 | Hotchkiss et al. | 428/198 |
| 4,469,734 | 9/1984 | Minto et al. | 428/134 |
| 4,519,798 | 5/1985 | Dinius | 604/358 |
| 4,537,822 | 8/1985 | Nanri et al. | 428/212 |

MULTILAYER NONWOVEN FABRIC

BACKGROUND OF THE INVENTION

The present invention relates to a nonwoven fabric having at least two layers of nonwoven web. More particularly, the present invention relates to a nonwoven fabric wherein at least one of the layers comprises a web having monofilaments or fibers with a bilobal cross-section as well as methods for making such multilayered nonwoven fabrics.

Nonwoven materials are, of course, well known in the art. Such materials were developed primarily in the 1950's and 1960's, although at least one reference dates back to 1943 (see, e.g., U.S. Pat. No. 2,336,743 to Manning).

One of the most significant commercial applications of nonwoven fabrics is in the fabrication of disposable products intended for a single use. Typical of such products are disposable diapers, feminine care products, surgical gowns, industrial wipes, and the like. Because the nonwoven fabric is intended as a cloth substitute in these applications, extensive effort has been expended to improve the properties of nonwoven fabric to more nearly approximate that of cloth. Of particular interest has been the softness of the nonwoven fabric, that is, improving the feel or "hand" of the fabric together with lowering the resistance of the web to folding or bending. Another important area has been the improvement of the nonwoven web's tensile strength or tear resistance. Yet another areas has been the development of nonwoven fabrics with specific wettability characteristics. With the few exceptions noted below, these efforts to improve the properties of nonwoven webs has focused almost exclusively on the use of fibers having a circular cross-section.

U S. Pat. No. 2,336,743 to Manning describes a method and apparatus for solution spinning or melt spinning nonwoven fabrics. According to the specification, the spinning material can be extruded through orifices in the spinneret, which orifices may be slits, circular, or of other cross-section.

U.S. Pat. No. 3,314,840 to Lloyd et al. relates to a process and apparatus for producing a nonwoven fabric. Although the disclosure appears to relate primarily to solution spinning, it does not appear to exclude melt spinning. The spinneret preferably has circular or slit openings, although such openings may have other shapes such as circles, triangles, crescents, etc.

U S. Pat. No. 3,508,390 to Bagnall et al. relates to a modified filament and fabrics produced therefrom. While the emphasis of the disclosure is on the preparation of conventional knitted fabrics, nonwoven fabrics are also mentioned. The filament has a cross-section consisting of three integrally joined, substantially symmetrical legs, thereby forming a substantially uniform Y-shaped cross-section having defined dimensions.

U.S. Pat. No. 3,509,009 to Hartmann relates to a nonwoven fabric which is prepared by meltspinning fiberforming high polymers into a directed gass current of high velocity to produce a uniform nonwoven fabric of great strength. While the filaments produced in accordance with the described invention are typically of circular cross-section, other cross-sections are mentioned, such as star-shaped, Y-shaped, or a combination thereof.

An apparatus for producing nonwoven fleeces is described in U.S. Pat. No. 3,528,129 also to Hartmann. The patent appears to be an improvement of an existing apparatus by specifying holes in the spinneret which have a branched cross-section. Y-shaped and T-shaped holes are specifically mentioned.

Finally, U.S. Pat. No. 3,630,816 to Parker relates to nonwoven sheets made from filaments having a rectangular cross-section. The rectangular cross-section of these filaments is specficed to have an aspect ratio of at least 3:1.

SUMMARY OF THE INVENTION

It is a general object of the present invention to provide a nonwoven fabric with improved softness and tensile strength. It is also a general object of the present invention to provide a method of producing such a nonwoven fabric. It is a more specific object of the present invention to provide a nonwoven liner for a disposable diaper which has improved softness, tensile strength, and moisture transfer capacity. It is another specific object of the present invention to provide a nonwoven wrap for a catamenial device which likewise has improved softness, tensile strength, and moisture transfer capacity.

These and other objects are accomplished by the present invention by providing a nonwoven fabric comprising at least two layers of nonwoven web. Each nonwoven web comprises a plurality of monofilaments of a thermoplastic material. In at least one of the webs the monofilaments have a bilobal cross-section. By the term "bilobal" the inventors intend to refer to a shape including an elongate and substantially rectangular portion which has at each of its furthest separated ends an enlarged portion which is typically circular and which enlarged portion has a diameter greater than the thickness of the rectangle. It has been found by the present inventors that a nonwoven web made with such bilobal shaped monofilaments provides remarkably increased softness as well as other desirable properties and particularly that such a "bilobal" web has many desirable properties when used in a multilayer structure.

In accordance with one of the preferred embodiments, the nonwoven fabric consists of two layers of a nonwoven web. The nonwoven web of the first layer comprises a plurality of substantially identically prepared continuous and substantially randomly deposited monofilaments of a thermoplastic polymer, which monofilaments have a bilobal cross-section. The nonwoven web of the second layer likewise comprises a plurality of substantially identically prepared continuous and substantially randomly deposited monofilaments of a thermoplastic polymer, with the exception that the monofilaments of the second layer most preferably have a trilobal or branched cross-section.

In addition, the nonwoven fabric of this preferred embodiment is stabilized by discrete compacted areas of thermally induced filament bonds extending through a major portion of both webs, with these compacted areas distributed in an intermittent regular pattern and constituting from about 10 to about 30 percent of the area of the fabric. Also in accordance with this preferred embodiment, the thermoplastic material is a polyolefin. Most preferably, the polyolefin is polypropylene, polyethylene, or an ethylene-propylene copolymer.

In accordance with another of the preferred embodiments, the nonwoven liner for a disposable diaper is constituted similarly to the preferred embodiment mentioned immediately above, with the stipulation that the first layer with bilobal filaments is intended to fit next to the wearer. Also, the second layer is used as a transfer layer to enhance the transfer of moisture through the nonwoven fabric and into the underlying absorbent material. This is accomplished by adding a wetting agent to the polyolefin monofilaments to thereby make the second layer which would otherwise be hydrophobic, somewhat hydrophillic or wettable. This addition can be done by mixing a wetting agent with the polymer before it is extruded or, more preferably, it can be done by applying a solution of the wetting agent to the nonwoven web after it is formed.

In accordance with still another of the preferred embodiments, the nonwoven wrap for a catamenial device is likewise oriented with the first layer next to the wearer. Also, the second or transfer layer is made wettable in the same manner as the preferred embodiment of the nonwoven liner for a disposable diaper.

In accordance with yet another of the preferred embodiments, the method of forming the nonwoven web of each layer includes the following steps. The polymer is preferably extruded while in a melted state through a spinneret plate with a multiplicity of holes with the desired cross-section, thereby producing a plurality of monofilaments with approximately the same cross-section. These monofilaments are then drawn, preferably pneumatically. After drawing, the monofilaments are laid down on a moving belt in an essentially random orientation with respect to each other.

At this point in the preferred method, the web of each layer can be joined to each other in one of the following three ways. The first and most preferable involves the use of parallel web formers, i.e. spinnerets together with drawing apparatus. In this way, the first former lays down a nonwoven web on a laydown belt just ahead of the point where the second former lays down its web. As a result, the second web is laid down on top of the first and the two continue through the remaining processing steps together. The two webs are then slightly compacted by passing through a pair of compaction rolls. Next, the two webs are bonded together and stabilized by passing through a pair of oppositely rotating heated rolls, the first of which has a smooth surface, and the second of which has a raised pattern. As a result, the two webs become thermally bonded in discrete areas arranged in a pattern which corresponds with the raised pattern of the one heated roller. Preferably, the pattern of thermally bonded areas is formed so as to constitute about 10 to about 30 percent of the surface of the nonwoven fabric.

The second method of joining also involves the use of two parallel formers as in the first, with the exception that the first laid down web passes through thermal bonding rolls as described above before the second web is laid on top of it. The two webs, i.e. one bonded and one not, are then slightly compacted and pass through a second pair of thermal bonding rolls. Preferably, in the interest of optimum softness, this second pair of thermal bonding rolls creates a bonded pattern in the two webs which occupies a lower percentage of multi-layer fabric than the bonded pattern of the first laid down web.

The third method of joining involves forming the first laid down web in a prior step and then winding it up. The fabric is then made by unrolling the first laid down web onto the belt on which the second laid down web is deposited. The two webs are then processed as described above.

DETAILED DESCRIPTION

In its broadest terms, the present invention comprehends a multilayer nonwoven fabric with at least two layers of nonwoven web, at least one of which comprises a plurality of monofilaments or fibers of a thermoplastic material, which monofilaments or filaments have a bilobal cross-section. In particular, the cross-sectional shape of these bilobal monofilaments can be described as including an elongate substantially rectangular portion which has at each of its furthest separated ends a substantially circular portion which has a diameter greater than the thickness of the rectangle. This shape could also be described as that of a "dogbone" or "dumbell".

In general, each web can be prepared from noncontinuous fibers, continuous monofilaments, or a combination thereof. The preferred method of producing each web is by spunbonding techniques, although meltblown techniques which produce noncontinuous fibers are also considered to be within the scope of this invention. At present, the continuous monofilaments produced by spunbonding techniques, are preferred.

The thermoplastic material of each web can either be the same or a different material from that of the other web. Each thermoplastic material must be capable of being spun into monofilaments. While it is contemplated to use spinnable materials such as glass, as a practical matter, it is preferred to use polymeric materials in both webs. Examples of such polymers, by way of illustration only, include polyolefins, polyamides, polyesters, polyurethanes, polyvinyl acetate, polyvinyl chloride, polyvinyl alcohol, polyacrylonitrile, polymethyl methacrylate, polyethyl acrylate, cellulose acetate, viscose, and the like. In addition, the thermoplastic material can be a homopolymer, a copolymer, or a blend or two or more polymers. At homopolymers, copolymers, and polymer blends of the polyolefins are preferred, with copolymers and homopolymers being more preferred. The most preferred homopolymers are polypropylene and polyethylene, and the most preferred co-polymer is an ethylene/propylene copolymer.

It is an important advantage of the present invention that certain materials which might not have optimum properties in a nonwoven web for various reasons, may be used in the present invention in combination with a web made from a different material to produce a better set of properties. For example, polyethylene is generally considered too soft and plastic for certain nonwoven web applications. However, in following the teaching of the present invention, a nonwoven web made from polyethylene can be bonded to a stronger nonwoven web, such as one made from polypropylene, to thereby make a more desirable web. At present, such a pairing is most preferred. That is, the most preferred embodiment comprises a nonwoven web made from polyethylene bonded to a nonwoven web made from polypropylene. This particular nonwoven fabric shows increases in both softness and tensile strength.

Figure 1:
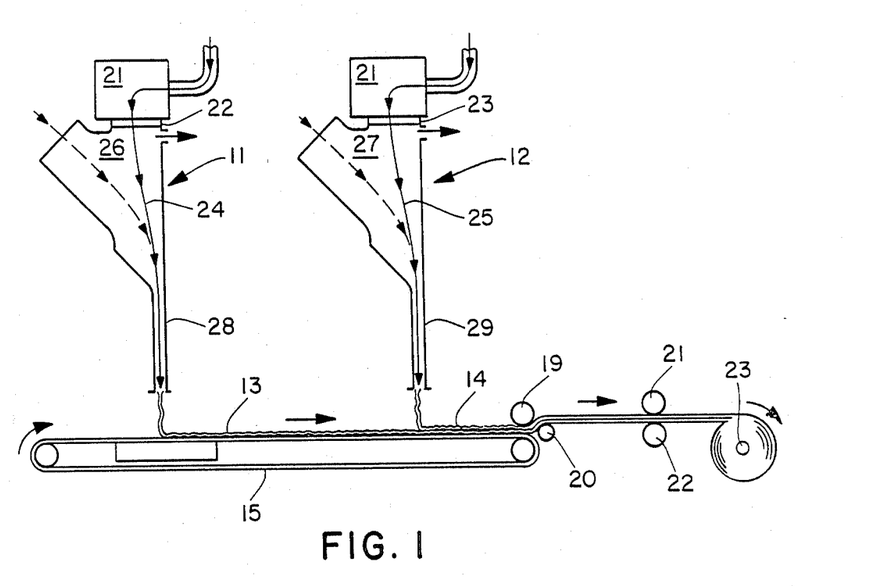
FIG. 1 is a schematic diagram of the preferred apparatus for producing the multilayered nonwoven fabric of the present invention.

FIG. 1 is a schematic diagram showing the preferred apparatus for forming such polymers into nonwoven webs. With one exception, this apparatus is made in accordance with the teachings of U.S. Pat. No. 4,405,297 and operated in accordance the teachings of U.S. Pat. No. 4,340,563, both to Appel and Morman, the entire disclosures of which are incorporated herein by reference. The exception is that instead of just one web former, i.e. spinneret and quenching/drawing apparatus, there are two such formers 11 and 12 in the fabrication line. The first former 11 lays down a first web 13 on the moving belt 15, while the second former 12 lays down a second web 14 on top of the first web 13.

While this is the preferred configuration for the web formers, other types of web formers are also available. For example, an alternative embodiment forms a nonwoven web with the apparatus and method described in U.S. Pat. No. 3,692,618, to Dorschner et al., the entire disclosure of which is also incorporated herein by reference.

Briefly, each of the nonwoven web formers 11 and 12 shown in FIG. 1 include a spinneret box 21 which receives a polymer in a melted state. As mentioned above, the polymer which goes into each web may or may not be the same. The temperature of each polymer melt is selected so as to make it sufficiently fluid for spinning. For example, when the polypropylene is being spun, the preferred temperature is about 460° F. When polyethylene is being spun, the preferred temperature is 375° F. Pressure is applied to each polymer melt to thereby push it through the holes or orifices in the spinneret plates 22 and 23 to thereby form the curtains of monofilaments 24 and 25 respectively. Each curtain 24 and 25 falls through a quench chamber 26 and 27 wherein it is contacted by quench air. The quench air in each former is supplied at a relatively low pressure, but such that there is sufficient pressure to also cause a degree of drawing of the monofilaments when they pass through the drawing nozzles 28 and 29.

Upon exiting the lower end of the drawing nozzle 28, the first curtain of monofilaments 24 is laid down on a moving foraminous surface 15, such as an endless screen or belt, to form a first nonwoven web 13. Upon exiting the lower end of the drawing nozzle 29, the second curtain of monofilaments 25 is laid down on top of the first nonwoven web 13 to form a second nonwoven web 14.

The two webs 13 and 14 then pass through a pair of compacting rollers 19 and 20 which slightly compact the filaments in the webs to thereby increase the integrity of the webs and to aid in further processing.

The two webs 13 and 14 next pass through the two heated bonding rolls 21 and 22. These rolls are preferably made and operated in accordance with the teachings of U.S. Pat. No. 3,855,046, to Hansen and Pennings, the entire disclosure of which is incorporated herein by reference. Briefly, the apparatus and process described therein includes the use of two rolls 21 and 22, at least one of which and preferably both of which are heated. The lower roll has a smooth surface while the upper roll 21 includes a raised intermittent pattern on its surface. In alternative embodiments, the bonding rolls can be reversed so that the roll with the pattern is under the web, thereby contacting the first laid web.

As the two webs 13 and 14 pass between these two heated rolls, each web becomes stabilized by the formation of discrete compacted areas of thermally induced filament bonds which extend through a major portion of the thickness of the web. These compacted areas are distributed in an intermittent pattern corresponding to the raised pattern of the roll 21 and provide unbonded filament spans therebetween. In addition, the two webs 13 and 14 become bonded together into the bilayered nonwoven fabric 18.

Figure 11A:
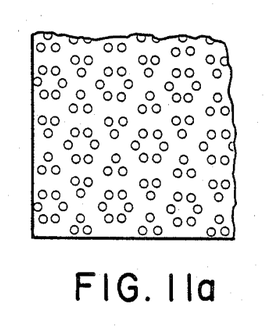
FIGS. 11a-c represent various patterns of intermittent heat bonding which can be applied to the nonwoven fabric of the present invention.
Figure 11B:
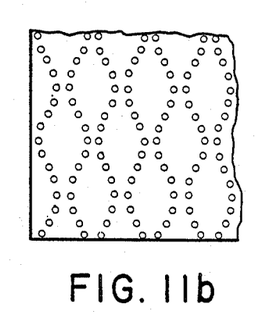
Figure 11C:
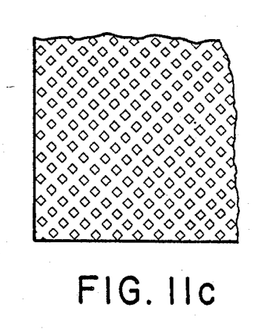

FIGS. 11a-c illustrate three patterns which can be used on the roll 21 and result in the same patterns on the nonwoven fabric 18. FIG. 11a includes circular areas arranged in hexagons and triangles. FIG. 11b includes circular areas arranged in a repeating hourglass configuration. FIG. 11c, which is the presently preferred pattern, includes equilateral diamond shaped areas which are arranged in staggered rows.

Two parameters of concern in regard to the specific pattern that is used are the size of the compacted areas formed and the distance between the areas. These two parameters together affect the percentage of area on the web which becomes bonded. It is important that the percentage of bonded area be great enough to insure sufficient integrity of the web for its intended use. In addition, it is important that the percentage of bonded area not be too great, as a higher bonded area usually produces a web with reduced softness. At present, it is preferred to have a bonded area between about 10 and about 30 percent of the surface area of the fabric. A range of about 12 to about 20 percent bonded area is more preferred, while about 17 percent is most preferred.

Another important factor relating to the bonding of the webs is the temperature at which the rolls 21 and 22 are maintained. Naturally temperatures below a certain point for each polymer will not effect any bonding, while temperatures above another point will melt too much of the web. Also, it has been observed the temperature of the rolls can affect both the tensile strength as well as the softness of the web produced. In particular, within a certain range, higher temperatures will produce a web with higher tensile strength. However, these same higher temperatures can produce a web with decreased softness. This is likely due to a higher and lower degree of bonding which occurs within this range of temperatures. That is, the higher temperatures likely result in a more and stronger interfilament bonding which is beneficial to tensile strength and somewhat detrimental to softness. At present, the preferred bonding temperature for polypropylene monofilaments is between about 220° and about 320° F. A temperature of about 275° F. is most preferred.

After the fabric 18 is bonded by rolls 21 and 22, it is wound on the take up roll 23. Alternatively, it may be desirable to design this apparatus to connect with a fabrication line for the end product.

The basis weight of the nonwoven fabric produced can be readily varied depending on the intended use of the web. For example, the nonwoven fabric can be made from about 0.3 to about 3 oz./square yard. Although in alternative embodiments, the basis weight of the first web may be made greater than that of the second, or vice versa, the preferred embodiment includes a first and second nonwoven web of equal basis weight. A preferred basis weight for a disposable diaper liner, i.e. with both layers, is about 0.8 oz./square yard and a preferred basis weight for a nonwoven wrap for a catamenial device is about 0.4 oz./square yard.

Figure 2:
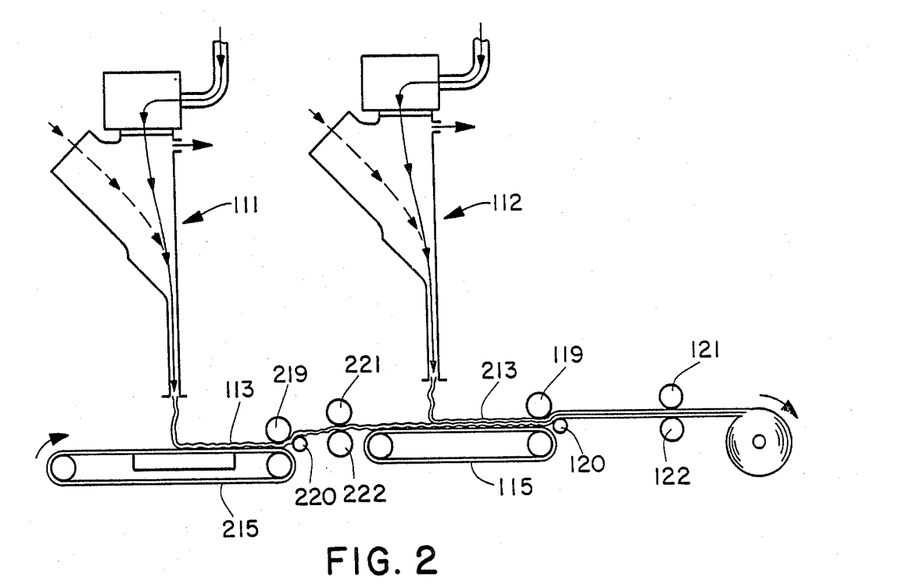
FIG. 2 is a schematic diagram of an alternative apparatus for producing the multilayered nonwoven fabric of the present invention.

FIG. 2 is a schematic diagram showing an alternative apparatus for producing the bilayered nonwoven fabric of the preferred embodiment. This apparatus is identical to the apparatus depicted in FIG. 1 with one exception. The exception is that between the first former 111 and the second former 112, there is included an additional pair of compaction rolls 119 and 120 together with an additional pair of bonding rolls 221 and 222 which stabilize the first web 113 in the manner discussed above. Also, instead of one collection belt 115, there is an additional belt 215 which picks up the first nonwoven web 113. These compaction and bonding rolls 219-222 are configured and operate the same as those described above with the exception that they are set for compacting and bonding a single nonwoven web.

After being compacted and bonded, the first nonwoven web 113 is picked up by the collection belt 115 after which the second nonwoven web 114 is laid down on top of it. The two nonwoven webs, i.e. the bonded web 113 and the unbonded web 114, pass through the compaction rollers 119 and 120. Next, they pass through the bonding rollers 121 and 122 where the second web 114 is stabilized and the two webs 113 and 114 become bonded together into a bilayered nonwoven fabric 118. The fabric 118 is then rolled up on the take up roll 123.

Figure 3:
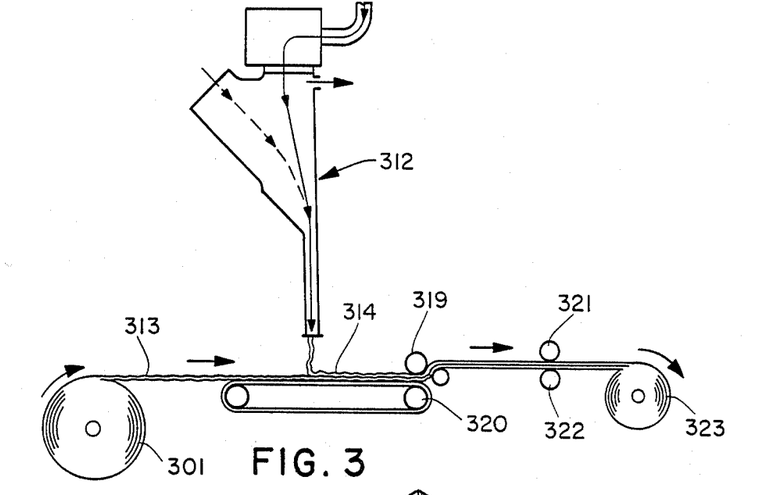
FIG. 3 is a schematic diagram of another alternative apparatus for producing the nonwoven fabric of the present invention.

FIG. 3 shows another alternative apparatus for producing the multilayered nonwoven fabric. In this apparatus, a first nonwoven web 313 is supplied from roll 301. At this point, the nonwoven web 313 can be either bonded or unbonded. Bonded is preferable. The web 313 passes along the collection belt 315 whereupon the second web 314 is laid on top of it. The two webs then pass through the compaction rolls 319 and 320 and then pass through the bonding rolls 321 and 322 where either both or just the second web becomes stabilized and the two webs 313 and 314 become bonded together as described above to form the bilayered nonwoven fabric 318.

In discussing the embodiments described in connection with FIGS. 2 and 3, it should be noted that, if the first laid down web is bonded before the second laid down web is placed upon it, the bond pattern used when the two webs are put together should be selected in consideration of the bond pattern already used on the first laid down web. It is desirable to have the second bond pattern not overlap the first. Therefore, if the second bonding pattern is the same as the first, it should be offset. However, in the interest of web softness, it is preferred to have the second bond pattern different from the first and particularly to occupy a lower percentage of the web than the first. Naturally, the final bond pattern through the first laid down web will be a sum of the first and second bonding. Accordingly, this also favors a lower percentage for the second bonding pattern.

As a point of clarification, it should be noted that the term first laid down web refers to the web which has been formed earlier in the processing line or alternatively to the web which has been made and rolled up in a previous step. It should also be noted that as used herein, and particularly in the claims, the terms "first web" and "second web" are arbitrary designations which do not necessarily refer to their order of forming. The order of laying each web and the particular polymer used will depend on the end use of the fabric.

It is an advantage of the present invention that the first laid down web can have a higher percentage area bonding pattern than the second laid down web. In this way, the first laid down web can possess sufficient tensile strength while the second laid down web can possess more softness. This is beneficial, for example, in a nonwoven web for a disposable diaper wherein the second laid down web can be used for increased softness on the "bodyside" of the diaper while the first laid down web can provide increased tensile strength for the liner.

Figures 4, 5, 6:
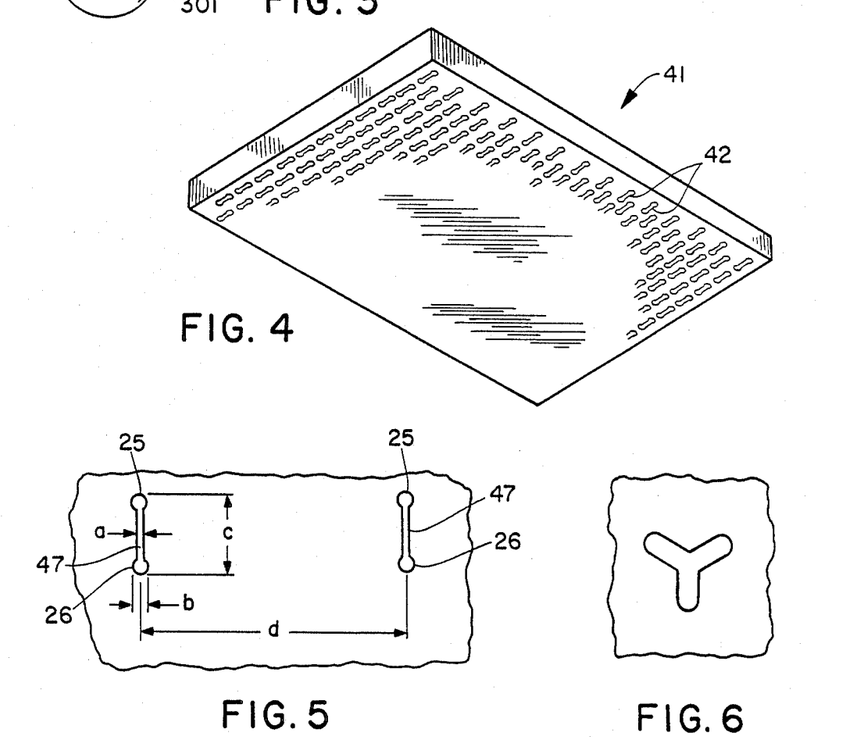
FIG. 4 shows a bottom perspective view of a spinneret plate with bilobal shaped orifices to thereby extrude monofilaments of bilobal cross-section.
FIG. 5 is a bottom and enlarged view of two of the bilobal shaped orifices of the spinneret plate of FIG. 4.
FIG. 6 is a bottom view of a trilobal shaped orifice in a spinneret plate.

FIG. 4 is a bottom perspective view of the spinneret plate 41 with bilobal shaped orifices 42. It is through these orifices 42 that the polymer is extruded. The monofilaments produced consequently have a cross-section with a bilobal, "dogbone" or "dumbell" shape. It has been found by the inventors that a multilayered nonwoven fabric produced with one of its layers being a nonwoven web with bilobal shaped monofilaments exhibits particular advantages.

Because the nonwoven fabric of this invention can be made with the bilobal monofilaments in either the first or the second laid down web, this bilobal spinneret plate can be in either of the formers shown in FIGS. 1-3. For reasons to be discussed below, it is presently preferred to place the bilobal spinneret plate in the second former of the apparatus described above. That is, it is presently preferred to have the monofilaments with the bilobal cross-section in the second laid down web.

The spinneret plate of the other former can have orifices of any desired shape. It is believed that having the bilobal monofilaments in one layer of the fabric provides at least some degree of improvement regardless of the shape of the monofilaments in the other layer. Circular orifices are, of course, most common and it is clearly contemplated to use circular monofilaments in one of the layers of the fabric. In addition, in certain embodiments it is desirable to have both layers of the fabric with bilobal monofilaments. At present, the most preferred shape of the cross-section of the monofilaments of the other, i.e. nonbilobal, web is referred to as Y-shaped. FIG. 6 shows a Y-shaped orifice for making such filaments.

The spinneret plate 12 is made with a width slightly greater than the width to be produced. The preferred width of the web will vary depending on the end use to made of it. For example, a nonwoven web made to be used as a liner for disposable diapers is preferably about 12.5 inches wide.

The number of orifices is selected and the orifices are arranged in the plate at the prescribed spacing in such a way so as to provide the desired density of filaments in the web. At present, it is preferred to have between about 30 and about 100 orifices in the spinneret plate per inch of web width. Most preferable is about 85 orifices per inch of web width. For examples, a 12 inch spinneret plate, i.e. one that will form a 12 inch wide nonwoven web, there are most preferably 1020 orifices.

FIG. 5 is an enlarged view showing the preferred configuration of two of the orifices 42 of the spinneret plate 41. The dimensions and proportions of the bilobal orifices are not known to be critical, provided that they produce monofilaments which have the bilobal shaped cross-section according to the present invention. Currently, the preferred configuration of the orifice is as follows. The shortest dimension is the thickness of the elongate portion a. The diameter b of the substantially circular portions 25 and 26 is approximately twice that of the thickness a. The length c of the orifice 24 is approximately ten times that of the thickness a. In the most preferred embodiment, the thickness a is 0.215 mm, the diameter b is 0.430 mm and the length c is 2.15 mm. Certainly, these dimensions and proportions can be varied in alternative embodiments depending on factors such as specific polymer which is extruded and the desired properties of the nonwoven web.

As mentioned, the preferred spacing between orifices will depend on the density of the nonwoven web to be produced. In the most preferred embodiment, the space d between orifices is 7.25 mm. Also, the preferred orientation of the orifices is such that all of the orifices are arranged parallel to each other and that their length c is aligned in the direction in which the belt 17 moves (i.e. machine direction).

FIG. 6 is bottom enlarged view of a Y-shaped orifice for a spinneret plate. The inventors have observed that monofilaments produced by this orifice retain a Y-shaped cross-section even after drawing. The inventors have also observed that nonwoven webs made with such Y-shaped monofilaments have increased stiffness, i.e. less softness than those made with circular or bilobal monofilaments. However, the inventors also observed that the web produced with Y-shaped monofilaments with increased tensile strength over those produced with circular monofilaments. As mentioned above, it is most preferred to have the nonbilobal layer be a web with Y-shaped monofilaments. This is currently thought to be desirable to obtain a fabric with both increased softness as well as increased tensile strength.

Figure 7:
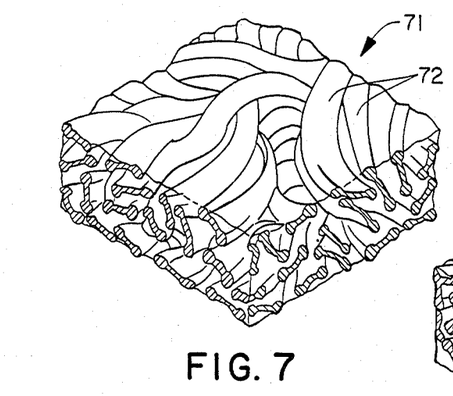
FIG. 7 is an illustration in partial cross-section of a nonwoven web with monofilaments of bilobal cross-section.

FIG. 7 is an illustration of a section of nonwoven web 71 made with bilobal monofilaments. This nonwoven web could be either the first or second laid down web in the processes described above, and would become part of the multilayer nonwoven fabric of the present invention. As can be seen the web comprises a number of continuous monofilaments 72 which are randomly oriented with respect to each other. It is desirable for the monofilaments to undergo a high degree of looping and overlapping in the web. These properties are influenced by factors such as the density of the monofilaments that are laid down, the speed at which the monofilaments are laid down, etc.

As can be seen, the monofilaments of this web 71 each have a bilobal cross-section. The dimensions of the bilobal cross-section are not known to be critical, provided that the basic features of such cross-section are present. That is, the cross-section of the monofilaments includes a substantially rectangular portion which has at each of its furthest separated ends an enlarged portion which typically is substantially circular.

As mentioned above, the monofilaments are drawn after being extruded through the spinneret plate 41. As a result, they typically have dimensions less than that of the orifices 42. The amount of this reduction will depend on factors such as the specific polymer extruded, the rate of quenching the monofilaments, the drawing force applied to the monofilaments, etc. In the preferred embodiment wherein polypropylene is used, the monofilaments typically end up with a cross-section length of between about 30 and about 60 microns. Most preferably, the cross-section length is about 40 microns, although this will vary depending on the desired properties of the nonwoven web.

Figure 8:
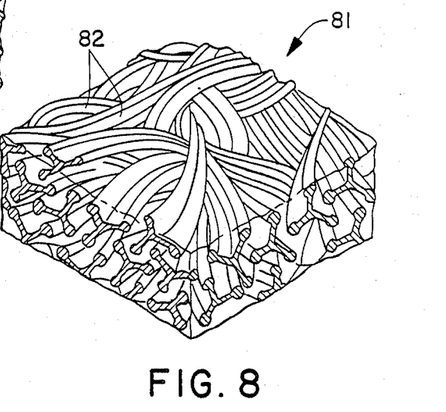
FIG. 8 is an illustration in partial cross-section of a nonwoven web with monofilaments of trilobal cross-section.

FIG. 8 is an illustration similar to that of FIG. 7 with the exception that the monofilaments shown have the Y-shaped cross-section. As mentioned, in the most preferred embodiment, one of the nonwoven webs would have this type of monofilaments.

Figure 9:
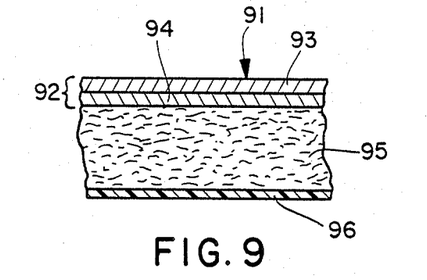
FIG. 9 is a cross-section of a portion of a disposable diaper made with the nonwoven liner of the present invention.

FIG. 9 is a cross-section through a disposable diaper 91. The nonwoven liner 92 is positioned on the side of the diaper 91 which will be placed next to the infant's body. As shown, the liner 92 consists of two layers 93 and 94. In the most preferred embodiment, the bodyside layer 93 comprises monofilaments with the bilobal cross-section, while the other layer 94 comprises monofilaments with the Y-shaped cross-section. Alternatively, the layer 94 can comprise bilobal monofilaments. The major portion of the diaper consists of a layer 95 of an absorbent material such as fluffed cellulose pulp. Naturally, this layer 95 is intended to absorb moisture. In addition, a moisture impermeable layer 96 is included.

An important property of the liner 92 is its softness. In particular, it is important for the liner 92 to be both extremely pliable as well as soft to the touch in consideration of the infant's comfort. The present inventors were somewhat surprised to observe that a nonwoven liner made with the bodyside layer comprising the monofilaments of bilobal cross-section exhibited remarkably improved softness over the prior art nonwoven liners made with monofilaments of circular cross-section.

One test which the inventors have used to evaluate the softness of nonwoven fabrics is called the "Smeltnik Stiffness Test". In this test a piece of nonwoven fabric is placed on top of an open cylinder. A hemispherical probe with a diameter slightly less than the inside diameter of the cylinder is then dropped from a standard height to thereby push the nonwoven fabric down into the cylinder. The distance that the probe travels into the cylinder is then measured and recorded as an indication of the softness, i.e. pliability or drapability of the fabric. As a comparison, while a nonwoven diaper liner made with circular monofilaments recorded a distance of 155 mm into the cylinder, a nonwoven diaper liner made with monofilaments of the same material but having a bilobal cross-section recorded a distance of 370 mm. Thus, a dramatic increase of the softness of the fabric was shown.

Another aspect of softness which is important particularly in diaper liners is the "hand" or softness to the touch. While a specific test for this property is not presently available to the inventors, they as well as others have observed an increased softness to the touch of the nonwoven web made with the monofilaments of bilobal cross-section, which web is preferably placed on the bodyside of the diaper 91.

Another property of a nonwoven liners and nonwoven fabrics in general is tensile strength, i.e. the resistance to tearing. This property has been measured by the present inventors on a device which grips a piece of a nonwoven fabric in a pair of jaws, and then pulls it apart. The force needed to break the fabric is recorded as the grab tensile strength. This test can be performed either with the fabric oriented in the jaws so that the force is applied parallel to the direction in which the fabric was laid down (machine direction, MD), or with the fabric is oriented so that the force is applied perpendicular to the direction in which the web was laid down (cross direction, CD). All of the values for tensile strength reported herein refer to machine direction (MD) strengths.

The inventors were pleased to observe that the nonwoven fabrics which had one layer of a nonwoven web with bilobal monofilaments showed increased tensile strength. While not wishing to be bound by any particular theory, it is currently believed that this increased tensile strength may be a result of the increased contact area available between filaments when they are thermally bonded as described above. Also, as mentioned above, the tensile strength of the multilayer fabric is increased when the first laid down web has a higher bonding area percentage. It is also believed that the tensile strength is improved when a bilobal web and Y-shaped web are used in a multilayer fabric, possibly due to the increased contact area for thermal bonding.

Yet another property which is particularly important when the web is used as a liner for a disposable diaper is the wettability of the liner. Depending on the design of the diaper, it is usually desirable to have the liner be at least partially wettable in order to facilitate passage of the moisture through to the absorbent layer. In addition, it is even more desirable to provide a wettability gradient in the liner whereby moisture can be wicked away from the wearer. In particular, it is most preferred to provide a bodyside layer which is less wettable than the "transfer" layer, i.e. the layer next to the absorbent material. In this way, moisture flows more easily through to the absorbent material than it flows back to the wearer.

Many of the polymers which are suitable to make nonwoven webs are hydrophobic. Specifically, the two most preferred polymers, polypropylene and polyethylene are completely hydrophobic. As a result, it is desirable to take steps to increase the wettability of nonwoven webs made with these polymers.

It is known in the art that wettability can be increased by the addition of wetting agents such as surfactants. Particularly, cationic, anionic, and nonionic surfactants may be added to materials to thereby make the material wettable. In one preferred embodiment of the present invention, the polypropylene monofilaments are made wettable by adding a nonionic surfactant to the monofilaments. This can be done by mixing the surfactant with the polymer before it is extruded, i.e. "internal addition". The wetting agent is preferably mixed with the polymer in an amount of up to about 5 percent by weight of the polymer. In addition, it has been found that with a polymer such as polypropylene, it is beneficial to heat the nonwoven web at some stage to thereby effect migration of the wetting agent to the surface of the monofilaments. Such a heating process which is used to bring an internally added lubricant to the monofilament surface is described in U.S. Pat. Nos. 3,973,068 and 4,070,218 to Weber, the entire disclosures of which are incorporated herein by reference. Naturally, the temperature to which the web is heated should be below the melting point of the monofilaments.

An advantage of the present invention is that it is possible to produce the described wettability gradient by adding the desired amount of wetting agent to the polymer which will go into the nonwoven web of the transfer layer. The web of the bodyside layer can either have no wetting agent, less wetting agent, or a less effective wetting agent added.

As an alternative to the internal application, the wetting agent can be applied in a solution to the nonwoven web after it is formed, i.e. "exterior application". This application can be carried out by dipping either each nonwoven web or both nonwoven webs together into a solution of the wetting agent, after which the solvent is evaporated to thereby leave an amount of the surfactant on the surface of the web or webs. It may also be desirable to heat the web to more quickly evaporate the solvent. Alternatively, the solution of surfactant may be applied to the web by spraying, or by rotogravure printing. In both cases, the evaporation of the solvent may be hastened by heating the web. Naturally, it is desirable for the evaporation to be complete before the web is wrapped on the wind up roll. In all three exterior application methods, the surfactant is applied so as to end up with up to about 5 percent by weight of the web.

As with internal application, it is preferable to selectively apply the wetting agent to produce a wettability gradient. This can be done by applying the wetting agent to either one or both of the webs before they are joined. Alternatively, it can be done by use of different materials in the webs so that the wetting agent is more effective when applied to the transfer layer than it is when applied to the bodyside layer.

The inventors observed that a web with Y-shaped monofilaments proved superior as a transfer layer than one with either bilobal or circular monofilaments. It is currently believed that this result is due to the increased bulk, i.e. lower density, of the web made with Y-shaped monofilaments which thereby provides a greater surface area for moisture absorption.

Still another property which is important in a nonwoven fabric for a liner is its opacity or hiding power. It is a known practice in the art to add minor amounts of titanium dioxide to the polymer melt in order to increase the opacity of nonwoven fabrics. The inventors have found that the nonwoven fabric produced according to the present invention has an increased opacity, possibly due to the increased surface area of the bilobal and/or Y-shaped monofilaments which could reflect more light.

Figure 10:
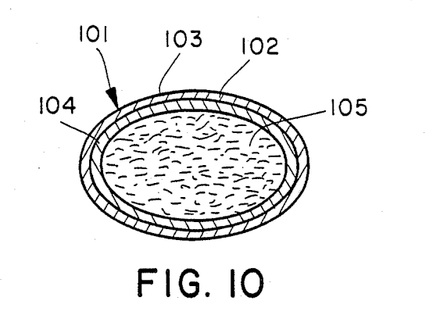
FIG. 10 is a partial cross-section of a catamenial device made with the nonwoven wrap of the present invention.

FIG. 10 shows a cross section through a typical catamenial device such as a feminine napkin 101. As shown, the pad consists of a nonwoven wrap 102 which surrounds an absorbent portion 105. The wrap consists of two nonwoven webs 103 and 104. Most of the properties which are desirable for the nonwoven liner for a disposable diaper are likewise desirable to have in the nonwoven wrap for a catamenial device. In particular, it is significant that the present invention provides a nonwoven web with increased softness, i.e. both drapability and smoothness to the touch. Accordingly, it is likewise preferred to have the web with the bilobal shaped monofilaments on the body side of the device. Also, it is typically important to enhance the wettability of the wrap 102, most preferably with a wettability gradient. This may be done by adding a wetting agent to the one or both of the webs in the wrap by methods such as those described in connection with the diaper liner above.

EXAMPLES

EXAMPLE 1 was run on an apparatus such as that described above in connection with FIG. 1. In particular, the web width was 12 inches and the first spinneret plate had 50 bilobal shaped orifices per inch of width and the second spinneret plate had 50 bilobal shaped orifices per inch of width. Polypropylene was extruded through the first spinneret at a melt temperature of about 460° F. Polypropylene was extruded through the second spinneret at a melt temperature of about 460° F. The basis weight of the first laid down web was 0.4 oz./square yard. The basis weight of the second laid down web was 0.4 oz./square yard. The two webs were bonded together with the pattern shown in FIG. 11a having a bonding area about 22.5 percent of the web area. The temperature of the bonding rolls was approximately 270° F.

The resultant fabric had a Smeltnik Stiffness Test (SST) value of 160 mm. In addition, the fabric of this example was measured for grab tensile strength by placing a piece of the web between oppositely pulling grippers. The force needed to tear the web was in the direction at which it was laid down (machine direction or MD) was 13 lbs.

EXAMPLE 2 was run similarly to Example 1 except that the apparatus used was that described in connection with FIG. 3. The first laid down web was bonded at about 270° F. with the pattern of 11a at about 22.5% bond area. The second web was laid down on top of the first laid web and then bonded with about 3% bond area. The first laid down web was made wettable by rotogravure printing a solution of nonionic surfactant.

The resultant fabric had an SST value of 200 mm, and a MD tensile strength of 10 lbs. In addition, a test was performed to measure the "run-off" value of this fabric. This test consists of placing an 8 to 10 inch piece of the web on top of an absorbent batt which were both oriented at a 45° angle. Then, 100 ml of water was poured onto the fabric at a point 6 inches from the bottom. The amount of water which ran off the bottom without being absorbed was measured and recorded. For Example 2, the value was 5.5 ml.

EXAMPLE 3 was run similarly to Example 2 except that the first laid layer was not bonded before the second was laid on top of it. The resultant fabric had an SST value of 315 mm, an MD tensile strength of 12 lbs., and a run-off value of 3.0.

EXAMPLE 4 was run similarly to Example 2 except that the first laid web was bonded at 250° F. before the second web was laid on top of it. The two webs were bonded together with a bond area of about 6.6%. The resultant fabric had an SST value of 430 mm, an MD tensile strength of 8 lbs., and a run-off value of 2.9 ml.

EXAMPLE 5 was run similarly to Example 2 except that the cross-section of the first laid web was Y-shaped and that the first laid web had a nonionic surfactant added internally. The two webs were bonded together at about 260° F. The resultant fabric had an SST value of 300 mm, an MD tensile strength of 6 lbs., and a run-off value (with the Y-shaped layer as the transfer layer) of 22.5.

EXAMPLE 6 was run similarly to Example 5 except that the first laid web had round monofilaments and the basis weight of the second laid web was 0.5 oz./square yard. The resultant fabric had an SST value of 220 mm, an MD tensile strength of 9 lbs., and a run-off value of 71 ml.

EXAMPLE 7 was run similarly to Example 2 except that the first laid layer and second laid layer each had a basis weight of 0.5. The monofilaments of the first laid layer were Y-shaped and had a nonionic surfactant added internally. The second layer was extruded through a spinneret plate with 30 orifices per inch. The final bonding temperature was about 280° F. The resultant fabric had an SST value of 230 mm, an MD tensile strength of 12 lbs., and a run-off value of 30 ml.

EXAMPLE 8 was run similarly to Example 1 except that polyethylene was extruded through the second spinneret with Y-shaped orifices at a melt temperature of about 375° F. The basis weight of the second laid web was 0.6 oz./square yard. The two webs were bonded together at about 225° F. with about 24% bond area. The resultant web had an SST value of 325 mm, and an MD tensile strength of 9.5 pounds.

While the invention has been described in connection with specific embodiments thereof, it is evident that many alternatives, modifications, and variations will be apparent to those skilled in the art in light of the foregoing description. In particular, although the nonwoven webs of the invention have been described in connection with liners for disposable diapers and with wraps for catamenial devices, other types of products such as surgical and other disposable garments, industrial wipes, and the like, are clearly contemplated. In addition, although the described embodiments have all had only two layers of nonwoven webs, fabrics with three or more layers are considered within the scope of the invention. Accordingly, it is intended to embrace all such alternatives, modifications, and variations as fall within the spirit and broad scope of the appended claims wherein the designation of first and second are arbitrary and not related to the order of forming or the position of the webs.

What is claimed is:

1. A multilayer nonwoven fabric comprising:
   a first nonwoven web comprising a first plurality of monofilaments or fibers of a first thermoplastic material, said monofilaments having a bilobal cross-section; and
   a second nonwoven web which is adjacent to and bonded to said first nonwoven web, said second nonwoven web comprising a second plurality of monofilaments or fibers of a second thermoplastic material.

2. The nonwoven fabric of claim 1 wherein said first and second thermoplastic materials are independently selected from the group consisting of polyolefins.

3. The nonwoven fabric of claim 2 wherein said polyolefin in said first nonwoven web is polypropylene.

4. The nonwoven fabric of claim 3 wherein said polyolefin of said second nonwoven web is polypropylene.

5. The nonwoven fabric of claim 3 wherein said polyolefin of said second nonwoven web is polyethylene.

6. The nonwoven fabric of claim 2 wherein said polyolefin in said first nonwoven web is polyethylene.

7. The nonwoven fabric of claim 6 wherein said polyolefin of said second nonwoven web is polypropylene.

8. The nonwoven fabric of claim 6 wherein said polyolefin of said second nonwoven web is polyethylene.

9. The nonwoven fabric of claim 2 wherein said polyolefin in one of said nonwoven webs is an ethylene-propylene copolymer.

10. The nonwoven fabric of claim 2 wherein the monofilaments or fibers of said second nonwoven web are more wettable than the monofilaments of said first nonwoven web.

11. The nonwoven fabric of claim 1 wherein the monofilaments or fibers of said second nonwoven web are more wettable than the monofilaments of said first nonwoven web.

12. The nonwoven fabric of claim 1 wherein the monofilaments or fibers of said second nonwoven web have a Y-shaped cross-section.

13. The nonwoven fabric of claim 12 wherein said first and second thermoplastic materials are independently selected from the group consisting of polyolefins.

14. The nonwoven fabric of claim 13 wherein said polyolefin in said first nonwoven web is polypropylene.

15. The nonwoven fabric of claim 14 wherein said polyolefin of said second nonwoven web is polypropylene.

16. The nonwoven fabric of claim 14 wherein said polyolefin of said second nonwoven web is polyethylene.

17. The nonwoven fabric of claim 13 wherein said polyolefin in said first nonwoven web is polyethylene.

18. The nonwoven fabric of claim 17 wherein said polyolefin of said second nonwoven web is polypropylene.

19. The nonwoven fabric of claim 17 wherein said polyolefin of said second nonwoven web is polyethylene.

20. The nonwoven fabric of claim 13 wherein said polyolefin in one of said nonwoven webs is an ethylene-propylene copolymer.

21. The nonwoven fabric of claim 13 wherein the monofilaments of said second nonwoven web are more wettable than the monofilaments of said first nonwoven web.

22. A multilayer nonwoven fabric comprising:
a first nonwoven web comprising a first plurality of substantially identically prepared continuous and substantially randomly deposited monofilaments of a first thermoplastic polymer, said monofilaments having a bilobal cross-section; and
a second nonwoven web which is adjacent to and bonded to the first nonwoven web, said second nonwoven web comprising a second plurality of substantially identically prepared continuous and substantially randomly deposited monofilaments of a second thermoplastic polymer.

23. The nonwoven fabric of claim 22 further comprising a degree of interfilament bonding in each of said nonwoven webs whereby said webs are stabilized.

24. The nonwoven fabric of claim 23 wherein said interfilament bonding comprises a plurality of discrete compacted areas of thermally induced filament bonds extending through a major portion of the thickness of the article, said compacted areas being distributed in an intermittent regular pattern and providing unbonded filament spans therebetween.

25. The nonwoven fabric of claim 24 wherein the compacted areas constitute from about 10 to about 30 percent of the area of the web.

26. The nonwoven fabric of claim 24 wherein the compacted areas constitute from about 12 to about 20 percent of the area of the web.

27. The nonwoven fabric of claim 24 wherein said first and second thermoplastic materials are independently selected from the group consisting of polyolefins.

28. The nonwoven fabric of claim 27 wherein said polyolefin in said first nonwoven web is polypropylene.

29. The nonwoven fabric of claim 28 wherein said polyolefin of said second nonwoven web is polypropylene.

30. The nonwoven fabric of claim 28 wherein said polyolefin of said second nonwoven web is polyethylene.

31. The nonwoven fabric of claim 27 wherein said polyolefin in said first nonwoven web is polyethylene.

32. The nonwoven fabric of claim 31 wherein said polyolefin of said second nonwoven web is polypropylene.

33. The nonwoven fabric of claim 31 wherein said polyolefin of said second nonwoven web is polyethylene.

34. The nonwoven fabric of claim 27 wherein said polyolefin in one of said nonwoven webs is an ethylene-propylene copolymer.

35. The nonwoven fabric of claim 27 wherein the monofilaments of said second nonwoven web are more wettable than the monofilaments of said first nonwoven web.

36. The nonwoven fabric of claim 24 wherein the monofilaments of said second nonwoven web are more wettable than the monofilaments of said first nonwoven web.

37. The nonwoven fabric of claim 24 wherein the monofilaments of said second nonwoven web have a trilobal cross-section.

38. The nonwoven fabric of claim 37 wherein said first and second thermoplastic materials are independently selected from the group consisting of polyolefins.

39. The nonwoven fabric of claim 38 wherein said polyolefin in said first nonwoven web is polypropylene.

40. The nonwoven fabric of claim 39 wherein said polyolefin of said second nonwoven web is polypropylene.

41. The nonwoven fabric of claim 39 wherein said polyolefin of said second nonwoven web is polyethylene.

42. The nonwoven fabric of claim 38 wherein said polyolefin in said first nonwoven web is polyethylene.

43. The nonwoven fabric of claim 42 wherein said polyolefin of said second nonwoven web is polypropylene.

44. The nonwoven fabric of claim 42 wherein said polyolefin of said second nonwoven web is polyethylene.

45. The nonwoven fabric of claim 38 wherein said polyolefin in one of said nonwoven webs is an ethylene-propylene copolymer.

46. The nonwoven fabric of claim 38 wherein the monofilaments of said second nonwoven web are more wettable than the monofilaments of said first nonwoven web.

47. A nonwoven diaper liner which comprises
a first nonwoven web comprising a first plurality of substantially identically prepared continuous and substantially randomly deposited monofilaments of a thermoplastic polymer, said monofilaments having a bilobal cross-section;

a second nonwoven web adjacent to and bonded to said first nonwoven web and comprising a second plurality of substantially identically prepared continuous and substantially randomly deposited monofilaments of a second thermoplastic polymer;

said liner having a plurality of discrete compacted areas of thermally induced filament bonds extending through a major portion of the thickness of both nonwoven webs, said compacted areas being distributed in an intermittent pattern providing unbonded filament spans therebetween.

48. The nonwoven diaper liner of claim 47 wherein the compacted areas constitute from about 5 to about 30 percent of the area of the diaper liner.

49. The nonwoven diaper liner of claim 47 wherein said second nonwoven web is more wettable than said first nonwoven web.

50. A nonwoven wrap for a catamenial device which comprises:

a first nonwoven web comprising a first plurality of substantially identically prepared continuous and substantially randomly deposited monofilaments of a thermoplastic polymer, said monofilaments having a bilobal cross-section;

a second nonwoven web adjacent to and bonded to said first nonwoven web and comprising a second plurality of substantially identically prepared continuous and substantially randomly deposited moncfilaments of a second thermoplastic polymer;

said nonwoven wrap having a plurality of discrete compacted areas of thermally induced filament bonds extending through a major portion cf the thickness of the both nonwoven webs, said compacted areas being distributed in an intermittent pattern providing unbonded filament spans therebetween.

51. The nonwoven diaper liner of claim 50 wherein the compacted areas constitute from about 5 to about 30 percent of the area of the diaper liner.

52. The nonwoven diaper liner of claim 51 wherein said second nonwoven web is more wettable than said first nonwoven web.

53. In an absorbent article which comprises a liner, and an absorbent material, the improvement comprising:

a first nonwoven web comprising a first plurality of substantially identically prepared continuous and substantially randomly deposited monofilaments of a thermoplastic polymer, said monofilaments having a bilobal cross-section;

a second nonwoven web adjacent to and bonded to said first nonwoven web and comprising a second plurality of substantially identically prepared continuous and substantially randomly deposited monofilaments of a second thermoplastic polymer;

said liner having a plurality of discrete compacted areas of thermally induced filament bonds extending through a major portion of the thickness of both nonwoven webs, said compacted areas being distributed in an intermittent pattern providing unbonded filament spans therebetween.

54. The improvement of claim 53 wherein the compacted areas constitute from about 5 to about 30 percent of the area of the web.

* * * * *